(12) United States Patent
Echegoyen et al.

(10) Patent No.: US 9,856,272 B2
(45) Date of Patent: Jan. 2, 2018

(54) [1-3]-THIAZINE-FULLEROPYRROLO DERIVATIVES OF C60 AND C70 AS HIV-INHIBITOR AGENTS

(71) Applicants: Luis A. Echegoyen, El Paso, TX (US); Danisha M. Rivera-Nazario, El Paso, TX (US); Edison A. Castro Portillo, El Paso, TX (US); Zachary Martinez, El Paso, TX (US); Manuel Llano, El Paso, TX (US)

(72) Inventors: Luis A. Echegoyen, El Paso, TX (US); Danisha M. Rivera-Nazario, El Paso, TX (US); Edison A. Castro Portillo, El Paso, TX (US); Zachary Martinez, El Paso, TX (US); Manuel Llano, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/343,631

(22) Filed: Nov. 4, 2016

(65) Prior Publication Data
US 2017/0197987 A1    Jul. 13, 2017

Related U.S. Application Data
(60) Provisional application No. 62/251,732, filed on Nov. 6, 2015.

(51) Int. Cl.
C07D 513/04 (2006.01)
C07D 519/00 (2006.01)

(52) U.S. Cl.
CPC .......... *C07D 513/04* (2013.01); *C07D 519/00* (2013.01)

(58) Field of Classification Search
CPC .................. C07D 513/04; C07D 519/00
See application file for complete search history.

(56) References Cited

FOREIGN PATENT DOCUMENTS

WO    WO 2016145134 A1 *  9/2016 ........... A61K 31/403

OTHER PUBLICATIONS

Journal of Medicinal Chemistry (2016), 59(24), 10963-10973.*
Barre-Sinossi et al., "Isolation of a T-lymphotropic retrovirus from a patient at risk for acquired immune deficiency syndrome (AIDS)." *Science*, vol. 220, 1983, pp. 868-870.
Clavel et al., "Isolation of a new human retrovirus from West African patients with AIDS." *Science*, vol. 223, 1986, pp. 343-346.
Klatzmann et al., "T-lymphocyte T4 molecule behaves as the receptor for human retrovirus LAV." *Nature*, vol. 312, 1984, pp. 767-768.
Gallo et al., "Frequent detection and isolation of cytopathic retroviruses (HTLV-III) from patients with AIDS and at risk for AIDS." *Science*, vol. 224, 1984, pp. 500-503.
Guyader et al., "Genome organization and transactivation of the human immunodeficiency virus type 2." *Nature*, vol. 326, 1987, pp. 662-669.
Maddon et al., "The T4 gene encodes the AIDS virus receptor and is expressed in the immune system and the brain." *Cell*, vol. 47, No. 3, 1986, pp. 333-348.
McDougal et al., "Binding of HTLV-III/LAV to T4+ T cells by a complex of the 110K viral protein and the T4 molecule." *Science*, vol. 231, 1986, pp. 382-385.
Varmus, "Retroviruses." *Science*, vol. 240, No. 4858, 1988, pp. 1427-1439.

* cited by examiner

*Primary Examiner* — Kahsay Habte
(74) *Attorney, Agent, or Firm* — Norton Rose Fulbright US LLP

(57) ABSTRACT

Certain embodiments useful as HIV-inhibitor agents are directed to fullerene derivatives tetrahydro-1H—$C_{60}$-fulleropyrrolo[1,2-c][1,3]thiazine salts (Formula I) or tetrahydro-1H—$C_{70}$-fulleropyrrolo[1,2-c][1,3]thiazine salts (Formula II), while further embodiments are directed to α, β, γ, and/or δ isomer of tetrahydro-1H—$C_{70}$-fulleropyrrolo[1,2-c][1,3]thiazine salt.

10 Claims, 13 Drawing Sheets

Simulated

Experimental

[1-3]-THIAZINE-FULLEROPYRROLO DERIVATIVES OF C60 AND C70 AS HIV-INHIBITOR AGENTS

This application claims priority to U.S. Application No. 62/251,732 filed Nov. 6, 2015, which is incorporated herein by reference in its entirety.

The invention was made with government support under Grant No. 5 SC1 AI098238-02 awarded by the National Institutes of Health and Grant No. CHE-14008865 awarded by the National Science Foundation. The government has certain rights in the invention.

BACKGROUND

The present invention relates generally to the field of medicine. More particularly, it concerns fullerene compositions and treatments using the same for HIV infection.

Human immunodeficiency virus (HIV) infects and destroys the immune system of human body. HIV infects $CD4^+$ T cells, a lymphocyte that activates our immune system against numerous infections. As the number of $CD4^+$ T cells in the body decrease, cell mediated immunity decreases and a HIV infected person develops acquired immunodeficiency syndrome (AIDS). An infected person becomes more susceptible to infections and cancers, even to those which rarely occur to a healthy individual.

The number of HIV infected individuals is increasing continuously over the years on a global scale, but currently there is no cure or effective vaccine against HIV virus. Currently highly active anti-retroviral therapy (HAART) is often used to treat AIDS. HAART consists of a combination of antiretroviral agents. Although HAART slows progression of the disease and decreases risk of death, adverse effects are very common due to large dose and long term administration. Moreover drug-resistant viruses and genomic mutation in HIV makes the therapy less effective over time.

Fullerenes have been valuable compounds in different fields and their functionalization has expanded their applications from biology to materials science. Particular attention has been given to their biological applications towards the inhibition of the human immunodeficiency virus (HIV). It is well known that $C_{60}$ and $C_{70}$ are capable of inhibiting HIV protease, presumably thru interactions with the hydrophobic cavity of the protease. These interactions are believed to be possible because the diameter of the HIV-protease cavity can host the $C_{60}$ or $C_{70}$ derivatives. It is not well understood what kinds of interactions dominate, not only because they will depend on the type of derivative but also because it has not been possible to prove that the fullerene-protease interactions indeed occur inside the cavity. Several research groups have used modeling software to study the possible fullerene derivative interactions with the HIV-protease and results suggest that it is likely to occur inside the cavity. From the latter results researchers have designed potential fullerene derivative candidates that can effectively interact with the HIV protease cavity and inhibit HIV infectivity.

Most of the current anti-HIV drugs are not effective after mutations of the virus occur. As a result, HIV becomes resistant to those drugs and infection of healthy cells follows. Alternative drugs for effective treatment of HIV are necessary to prevent its transmission and infection of healthy cells, especially after mutation occurs.

SUMMARY

Embodiments of the invention relate to the design of a new class of fullerene derivatives as biologically active materials against HIV. The Acquired Immunodeficiency Syndrome (AIDS) caused by the Human Immunodeficiency Virus (HIV) has spread worldwide since its discovery. The effects of this contagious disease in the health and economy of both developed and under-developed countries are outrageous. Therefore, immeasurable efforts to discover and/or design and synthesize biologically active materials that can work as anti-HIV agents are being expended by scientists worldwide.

The two main anti-HIV agents for HIV growth are those that target the HIV reverse transcriptase and those that inhibit the HIV-protease. It has been shown in the literature that specific [60]-fullerene derivatives actively interact and inhibit the HIV-protease.

Described herein is the design, synthesis, and characterization of quaternary salts of [1,3]thiazine [60]- and [70]-fulleropyrrolo derivatives (Schemes 1 and 2, FIG. 11 and FIG. 12, respectively) as a new class of anti-HIV agents aiming for alternative treatments for the disease.

The reaction conditions to obtain the [70]-fullerene derivatives are followed as for the synthesis of the [60]-fullerene derivatives. While for $C_{60}$ there is only one possible regioisomer for the mono-adduct derivatives, for $C_{70}$ it is possible to obtain a mixture of three mono-regioisomers (α, β, γ) but a fourth (δ) can possibly be obtain as well in significantly lower yields.

As for the disclosure, the quaternary ammonium salts of isolated pure mono- and bis-regioisomers of $C_{60}$ and $C_{70}$ and regioisomeric mixtures of mono-, bis- and tris-regioisomers of $C_{60}$ and $C_{70}$ are disclose as biologically active materials for HIV inhibition and other applications.

Certain embodiments are directed to $C_{60}$ fullerene derivatives tetrahydro-1H—$C_{60}$-fulleropyrrolo[1,2-c][1,3]thiazine salt derivatives (Formula I, FIG. 13) or tetrahydro-1H—$C_{70}$-fulleropyrrolo[1,2-c][1,3]thiazine salt derivatives (Formula II, FIG. 14). Representative formulas are provided as Formula I and Formula II where n can be 1, 2, or 3.

Certain embodiments are directed to administration of one or both of tetrahydro-1H—$C_{60}$-fulleropyrrolo[1,2-c][1,3]thiazine salt derivatives (Formula I) or tetrahydro-1H—$C_{70}$-fulleropyrrolo[1,2-c][1,3]thiazine salt derivatives (Formula II) to treat and reduce HIV infection. The fullerene derivative(s) can be administered alone or in combination with each other or other anti-cancer therapies.

In certain aspects an tetrahydro-1H—$C_{60}$-fulleropyrrolo[1,2-c][1,3]thiazine salt is administered to treat and reduce HIV infection. The tetrahydro-1H—$C_{60}$-fulleropyrrolo[1,2-c][1,3]thiazine salt can be administered alone or in combination with one or more additional anti-HIV therapies.

In certain aspects an tetrahydro-1H—$C_{70}$-fulleropyrrolo[1,2-c][1,3]thiazine salt is administered to treat and reduce HIV infection. The tetrahydro-1H—$C_{70}$-fulleropyrrolo[1,2-c][1,3]thiazine salt can be administered alone or in combination with one or more additional anti-HIV therapies.

In a further aspect an α isomer of tetrahydro-1H—$C_{70}$-fulleropyrrolo[1,2-c][1,3]thiazine salt is administered to treat and reduce HIV infection. The α isomer of tetrahydro-1H—$C_{70}$-fulleropyrrolo[1,2-c][1,3]thiazine salt can be administered alone or in combination with one or more additional anti-HIV therapies.

In a further aspect β isomer of tetrahydro-1H—$C_{70}$-fulleropyrrolo[1,2-c][1,3]thiazine salt is administered to treat and reduce HIV infection. The β isomer of tetrahydro-1H—$C_{70}$-fulleropyrrolo[1,2-c][1,3]thiazine salt can be administered alone or in combination with one or more additional anti-HIV therapies.

In an another aspect γ isomer of tetrahydro-1H—$C_{70}$-fulleropyrrolo[1,2-c][1,3]thiazine salt is administered to treat and reduce HIV infection. The γ isomer of tetrahydro-1H—$C_{70}$-fulleropyrrolo[1,2-c][1,3]thiazine salt can be administered alone or in combination with one or more additional anti-HIV therapies.

In an another aspect δ isomer of tetrahydro-1H—$C_{70}$-fulleropyrrolo[1,2-c][1,3]thiazine salt is administered to treat and reduce HIV infection. The δ isomer of tetrahydro-1H—$C_{70}$-fulleropyrrolo[1,2-c][1,3]thiazine salt can be administered alone or in combination with one or more additional anti-HIV therapies.

In an another aspect a mixture of tetrahydro-1H—$C_{70}$-fulleropyrrolo[1,2-c][1,3]thiazine salt isomers is administered to treat and reduce HIV infection. The mixture of tetrahydro-1H—$C_{70}$-fulleropyrrolo[1,2-c][1,3]thiazine salt isomers can be administered alone or in combination with other anti-HIV therapy. In certain aspects the mixture can comprise 5, 10, 20, 30, 30, 40, 50, 60, 70, 80, or 90%, including all values and ranges there between, of an α isomer of tetrahydro-1H—$C_{70}$-fulleropyrrolo[1,2-c][1,3]thiazine salt with respect to the total amount of tetrahydro-1H—$C_{70}$-fulleropyrrolo[1,2-c][1,3]thiazine salt. In a further aspect the mixture can comprise 5, 10, 20, 30, 30, 40, 50, 60, 70, 80, or 90%, including all values and ranges there between, of a β isomer of tetrahydro-1H—$C_{70}$-fulleropyrrolo[1,2-c][1,3]thiazine salt with respect to the total amount of tetrahydro-1H—$C_{70}$-fulleropyrrolo[1,2-c][1,3]thiazine salt. In still a further aspect the mixture can comprise 5, 10, 20, 30, 30, 40, 50, 60, 70, 80, or 90%, including all values and ranges there between, of a γ isomer of tetrahydro-1H—$C_{70}$-fulleropyrrolo[1,2-c][1,3]thiazine salt with respect to the total amount of tetrahydro-1H—$C_{70}$-fulleropyrrolo[1,2-c][1,3]thiazine salt. In still a further aspect the mixture can comprise 5, 10, 20, 30, 30, 40, 50, 60, 70, 80, or 90%, including all values and ranges there between, of a δ isomer of tetrahydro-1H—$C_{70}$-fulleropyrrolo[1,2-c][1,3]thiazine salt with respect to the total amount of tetrahydro-1H—$C_{70}$-fulleropyrrolo[1,2-c][1,3]thiazine salt.

In certain aspects one or more tetrahydro-1H—$C_{60}$-fulleropyrrolo[1,2-c][1,3]thiazine or tetrahydro-1H—$C_{70}$-fulleropyrrolo[1,2-c][1,3]thiazine salt isomer(s) are administered to a subject in need of an anti-HIV treatment. In certain aspects the isomers are administered within 1, 5, 10, 20, 30, or 60 minutes or hours of each other. In a further aspect the isomers are administered concurrently. In certain aspects the isomers are formulated in the same composition. In a further aspects the HIV patient has a second viral infection. The second viral infection can be, but is not limited to hepatitis B virus (HBV), hepatitis C virus (HCV), or cytomegalovirus (CMV).

Certain aspects include methods for treating an HIV co-infection in an HIV patient comprising administering to a patient an effective amount of a one or more isomers of tetrahydro-1H—$C_{60}$-fulleropyrrolo[1,2-c][1,3]thiazine salt or tetrahydro-1H—$C_{70}$-fulleropyrrolo[1,2-c][1,3]thiazine salt. The patient can be co-infected with hepatitis B virus, hepatitis C virus, cytomegalovirus, or other virus.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, etc.).

"Subject", "individual," "host" and "patient" are used interchangeably herein, to refer to any animal, e.g., mammal, human or non-human. Generally, the subject is a mammalian subject. Exemplary subjects include, but are not necessarily limited to, humans, non-human primates, cattle, sheep, goats, pigs, dogs, cats, and horses, with humans being of particular interest.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention.

Throughout this application, the term "about" is used to indicate that a value includes the inherent variation of error for the device, the method being employed to determine the value, or the variation that exists among the study subjects.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

As used herein, the term "IC50" refers to an inhibitory dose that results in 50% of the maximum response obtained.

The term half maximal effective concentration (EC50) refers to the concentration of a drug that presents a response halfway between the baseline and maximum after some specified exposure time.

The terms "inhibiting," "reducing," or "prevention," or any variation of these terms, when used in the claims and/or the specification includes any measurable decrease or complete inhibition to achieve a desired result.

The use of the term "or" in the claims is used to mean "and/or" unless explicitly indicated to refer to alternatives only or the alternatives are mutually exclusive, although the disclosure supports a definition that refers to only alternatives and "and/or."

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION

Figure 1:
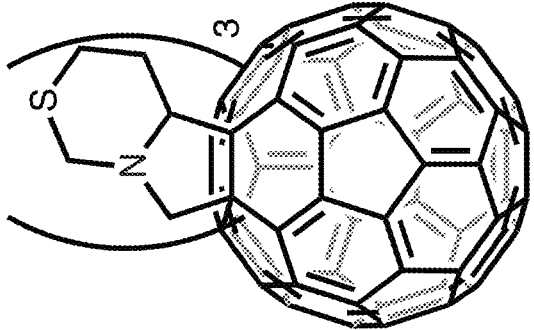
FIG. 1. Structure of [1,3]Thiazine[60]fulleropyrrolidine derivatives. Mono: DMRN-1; *bis: DMRN-2 and *tris: DMRN-3. *Regioisomeric mixture.
Figure 1:
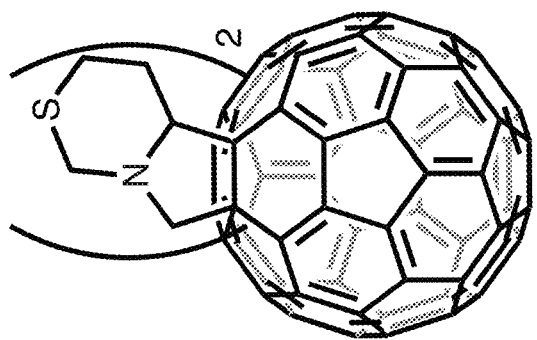
Figure 1:
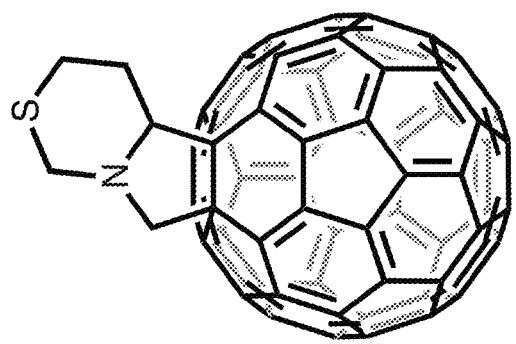
Figure 2:
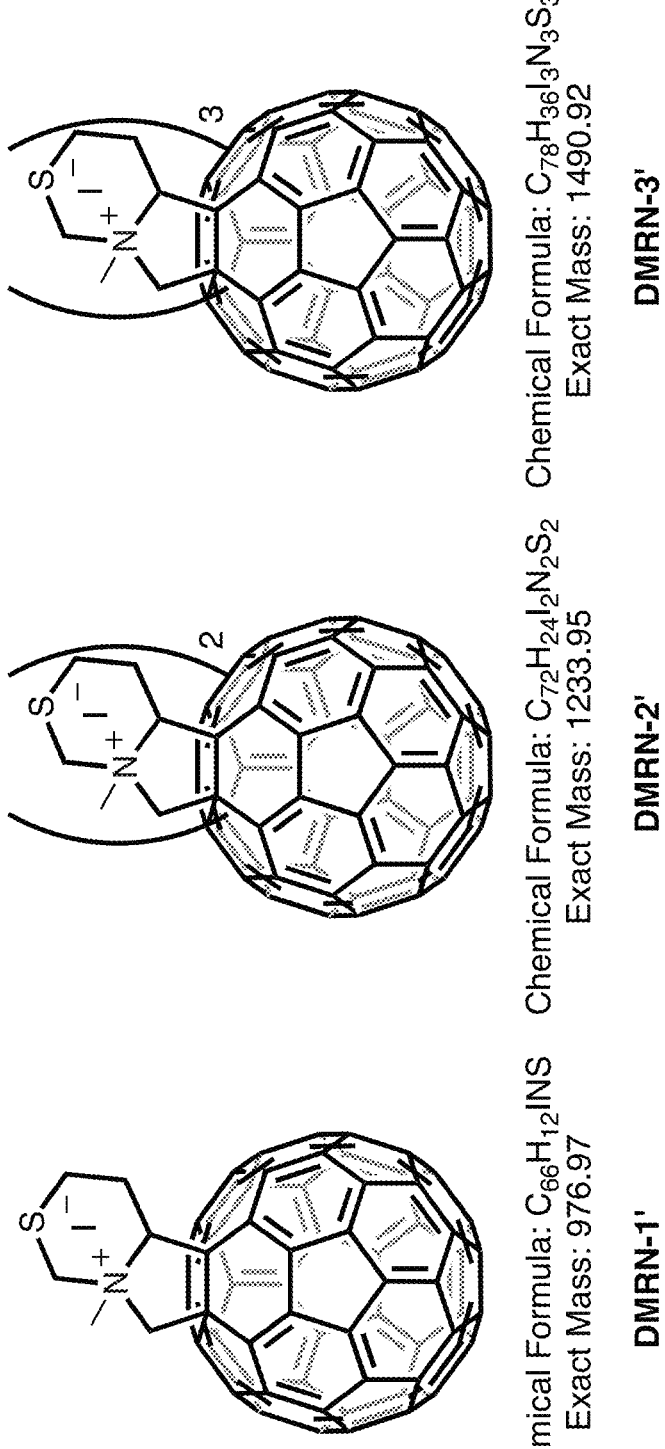
FIG. 2. Structure of [1,3]Thiazine[60]fulleropyrrolidinium salt derivatives. Mono: DMRN-1'; *bis: DMRN-2' and *tris: DMRN-3'. *Regioisomeric mixture.
Figure 3:
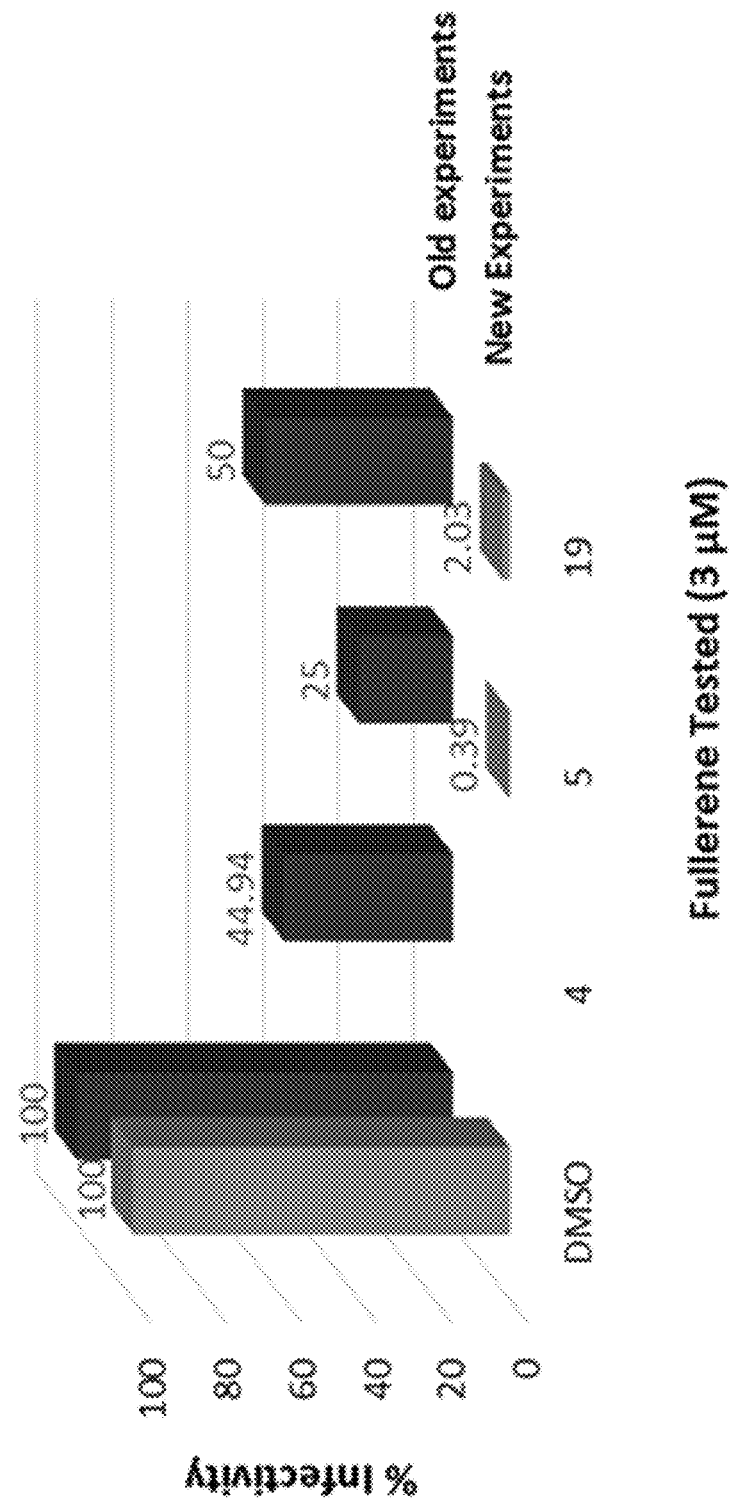
FIG. 3. Late stage HIV inhibition results (4=DMRN-1'; 5=DMRN-2'; 19=DMRN-3').
Figure 4:
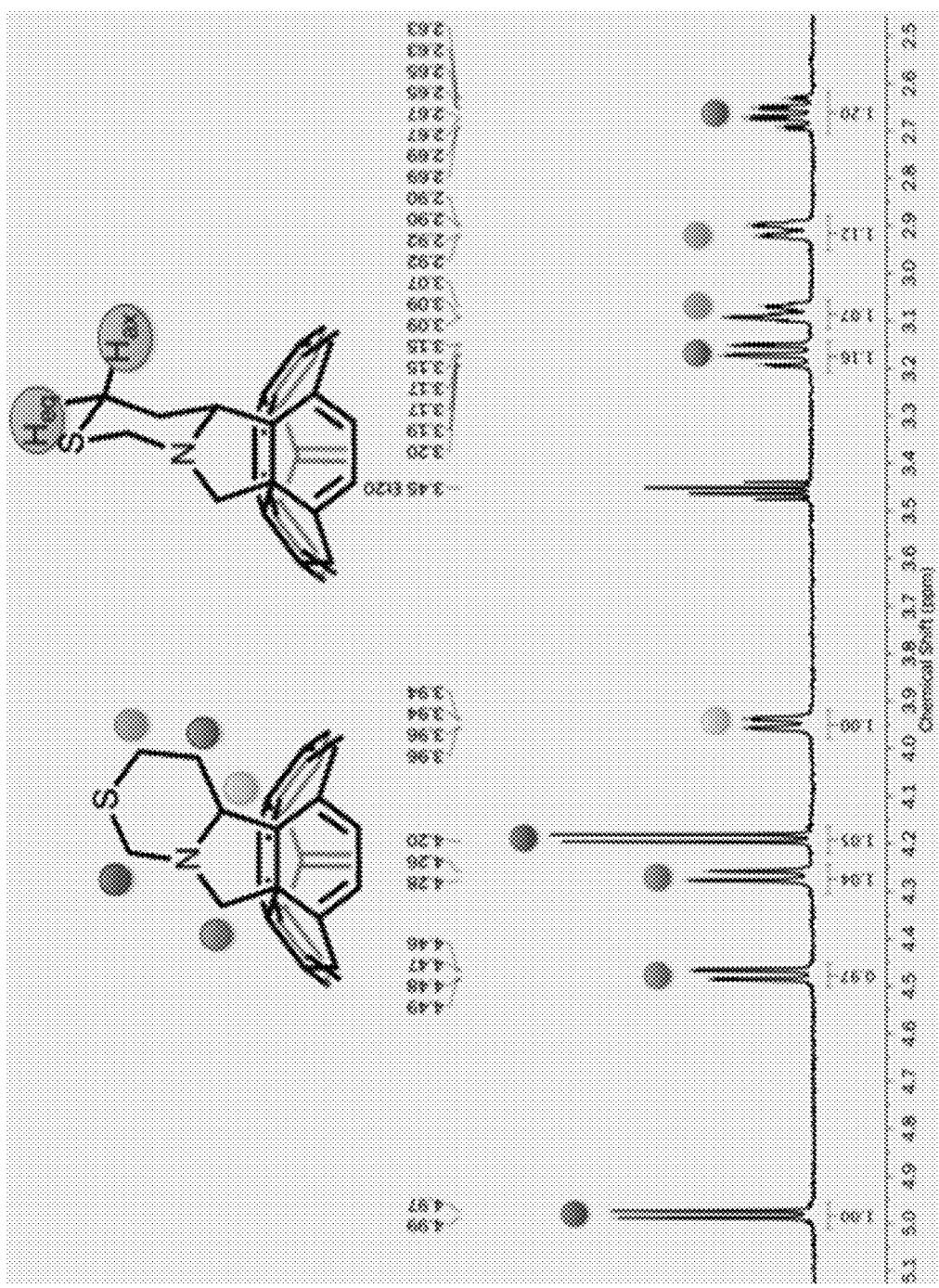
FIG. 4. $^1$H NMR of mono-[1,3]Thiazine[60]fulleropyrrolidine in $CS_2$:$CDCl_3$ at 600 MHz.
Figure 5:
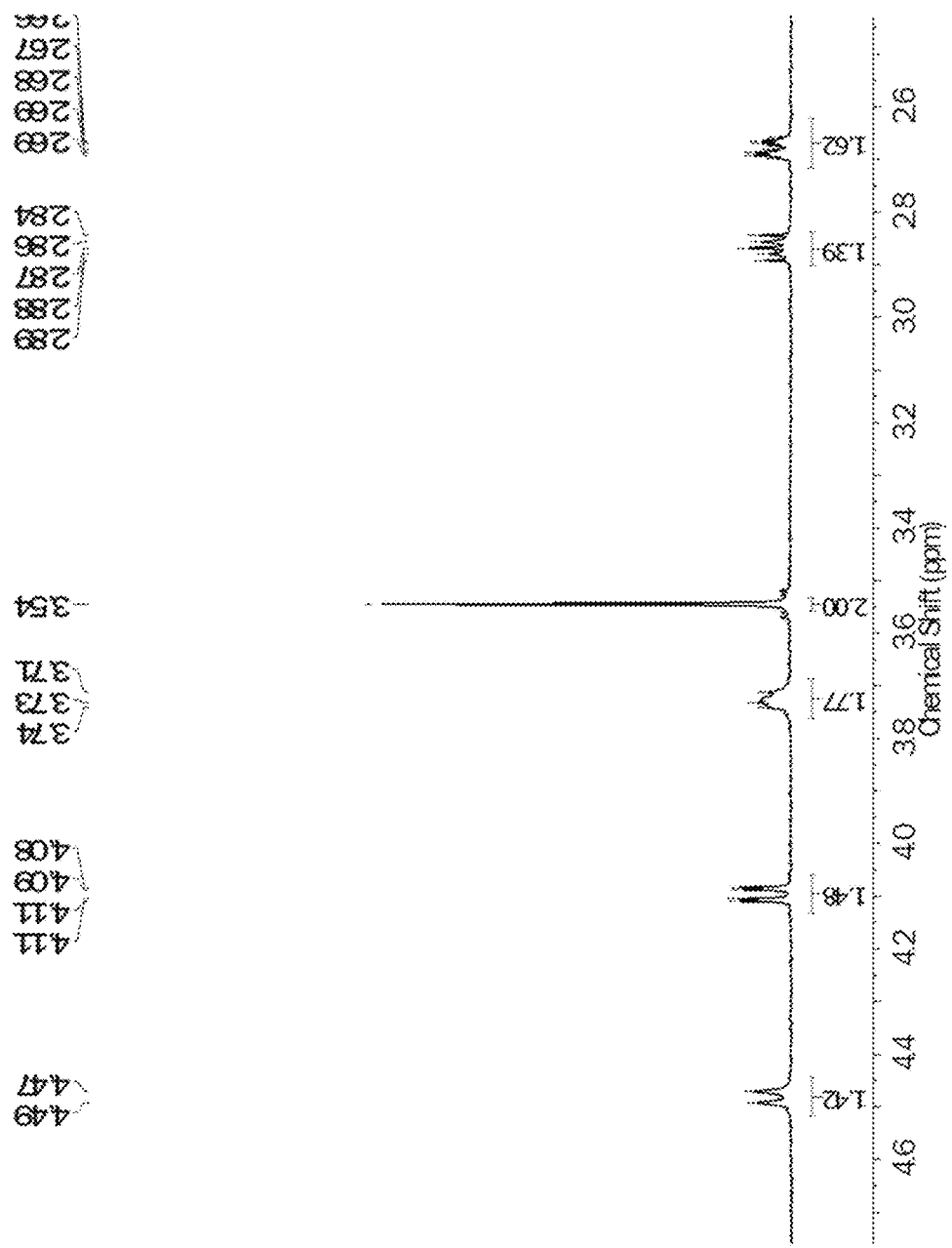
FIG. 5. $^1$H NMR of mono-[1,3]Thiazine[70]-$\gamma^1$-fulleropyrrolidine in $CS_2$:$CDCl_3$ at 600 MHz.
Figure 6:
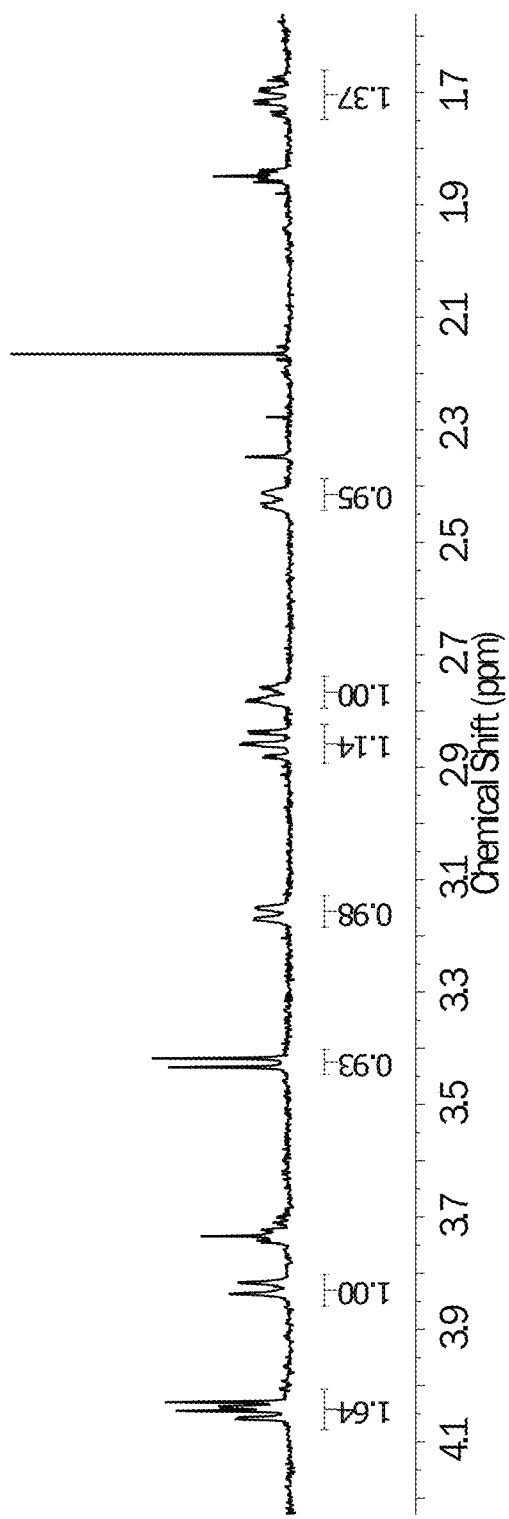
FIG. 6. $^1$H NMR of mono-[1,3]Thiazine[70]-$\beta^1$-fulleropyrrolidine in $CS_2$:$CDCl_3$ at 600 MHz.
Figure 7:
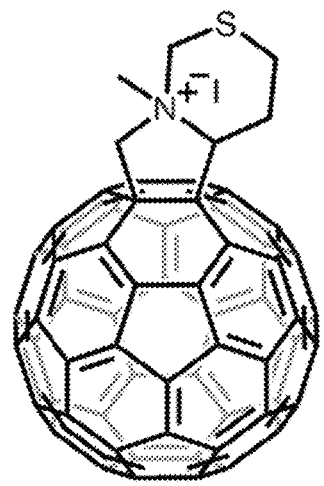
FIG. 7. MALDI-TOF MS (m/z): mono tetrahydro-1H—$C_{60}$-fulleropyrrolidinium[1,2-c][1,3]thiazine iodide.
Figure 7:
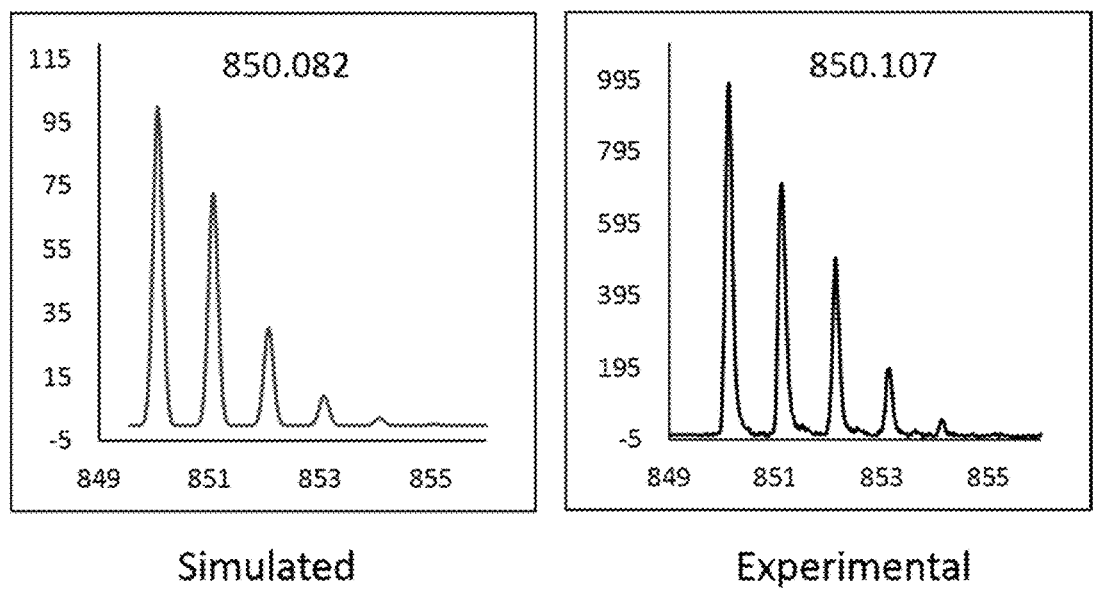
Figure 8:
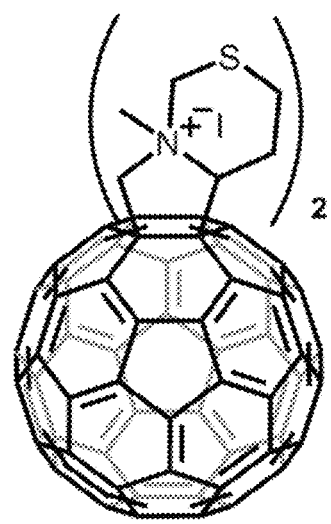
FIG. 8. MALDI-TOF MS (m/z): bis tetrahydro-1H—$C_{60}$-fulleropyrrolidinium[1,2-c][1,3]thiazine iodide.
Figure 8:
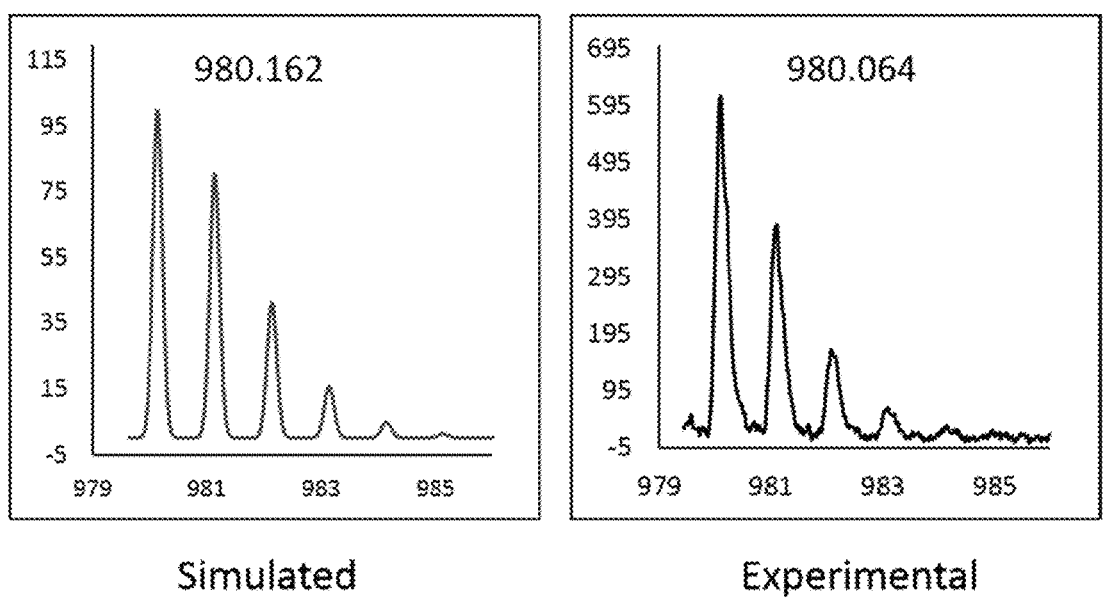
Figure 9:
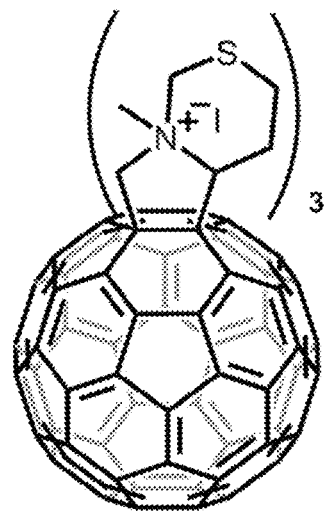
FIG. 9. MALDI-TOF MS (m/z): tris tetrahydro-1H—$C_{60}$-fulleropyrrolidinium[1,2-c][1,3]thiazine iodide.
Figure 9:
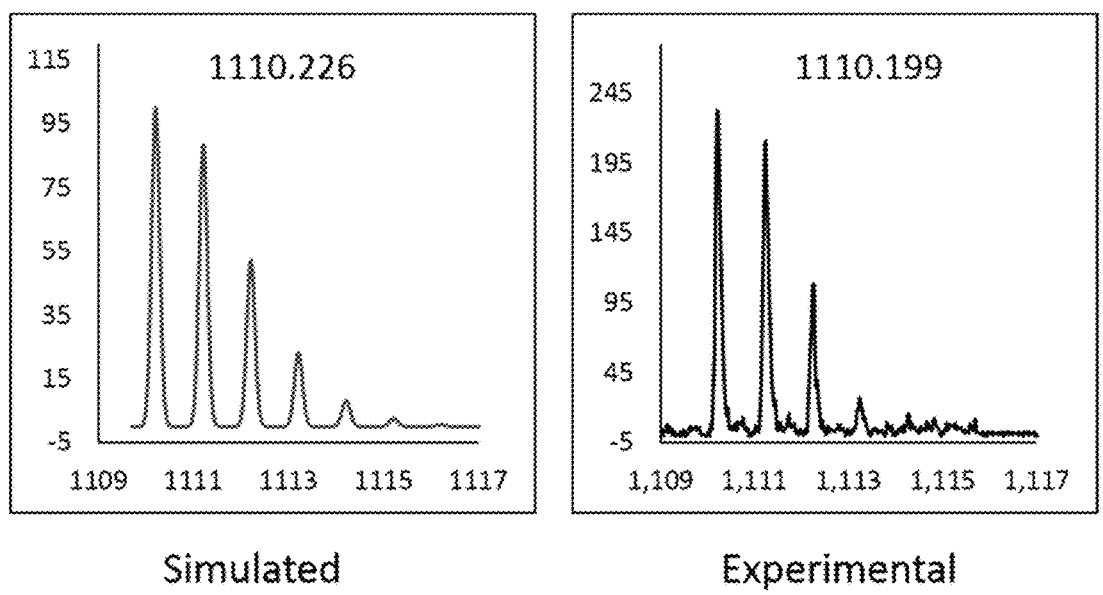
Figure 10:
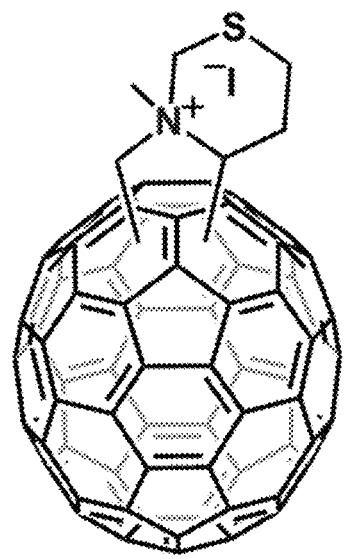
FIG. 10. MALDI-TOF MS mono (m/z): tetrahydro-1H—$C_{70}$-fulleropyrrolidinium[1,2-c][1,3]thiazine iodide.
Figure 10:
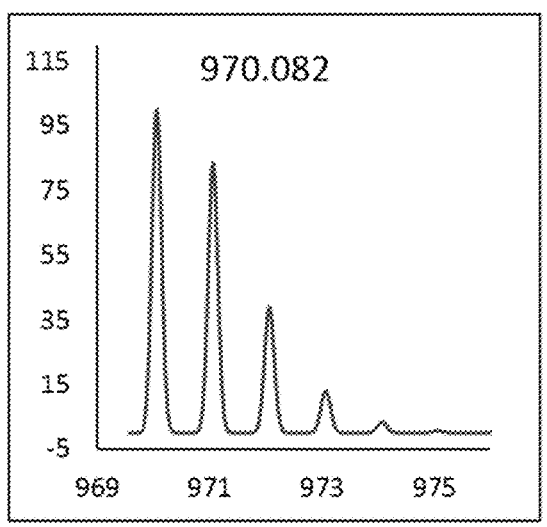
Figure 10:
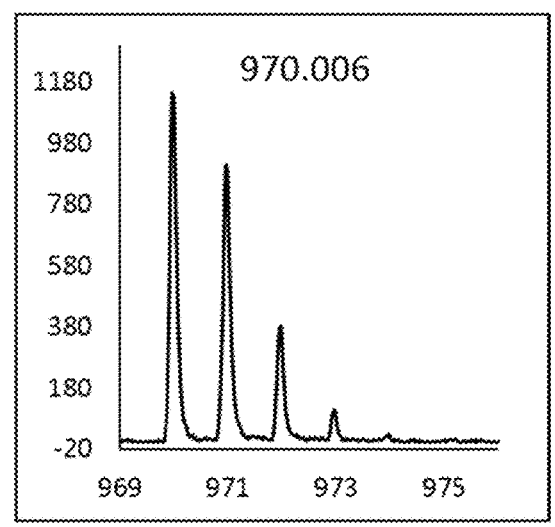
Figure 11:
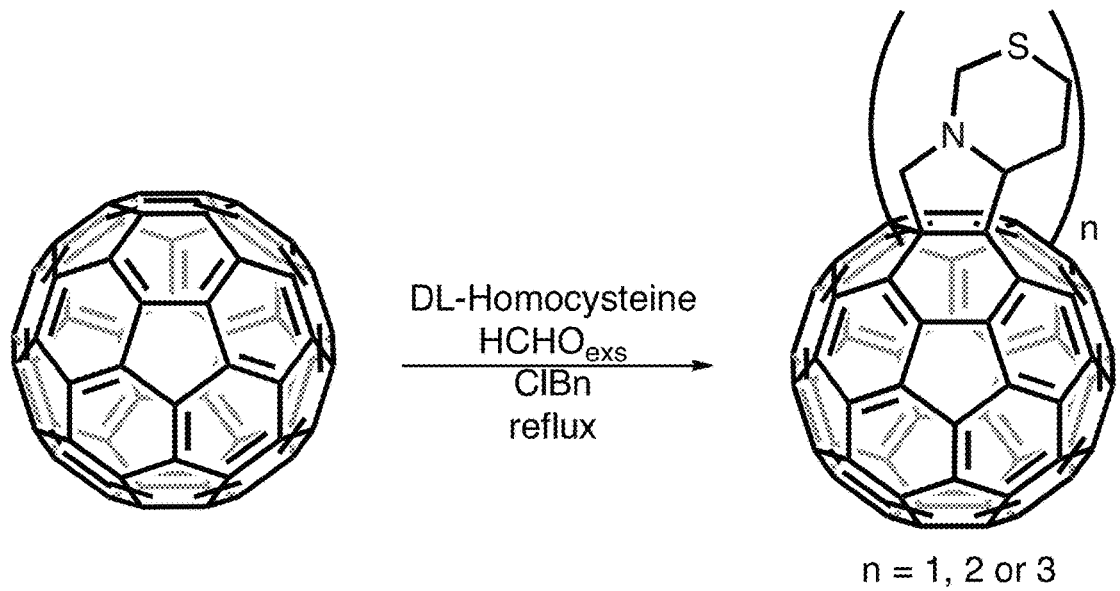
FIG. 11. Scheme 1. Synthesis of tetrahydro-1H—$C_{60}$-fulleropyrrolo[1,2-c][1,3]thiazine derivatives.
Figure 12:
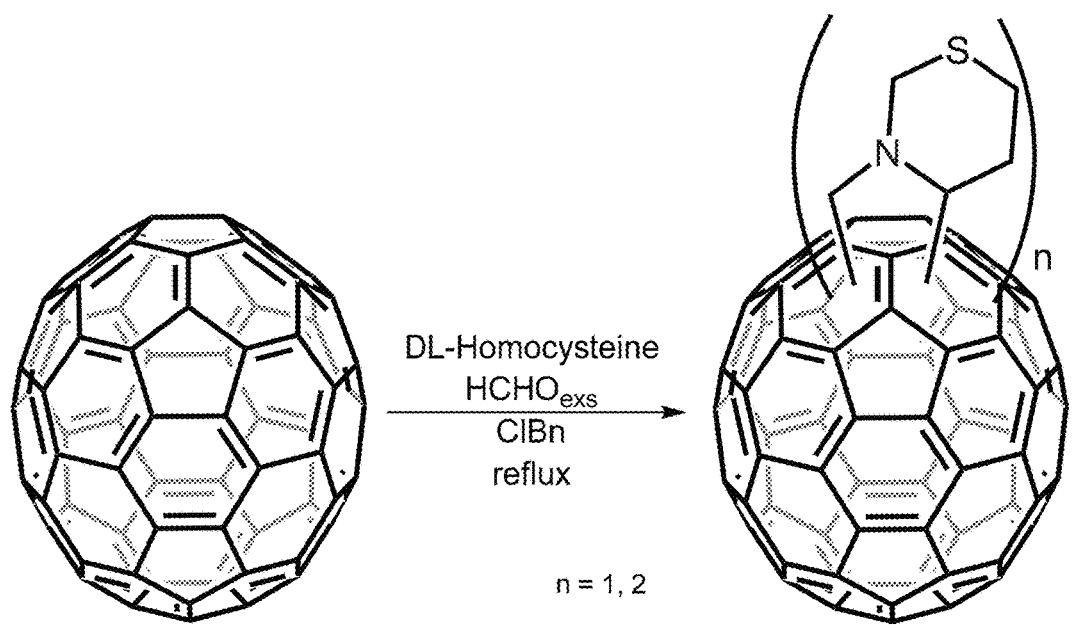
FIG. 12. Scheme 2. Synthesis of tetrahydro-1H—$C_{70}$-fulleropyrrolo[1,2-c][1,3]thiazine derivatives.
Figure 13:
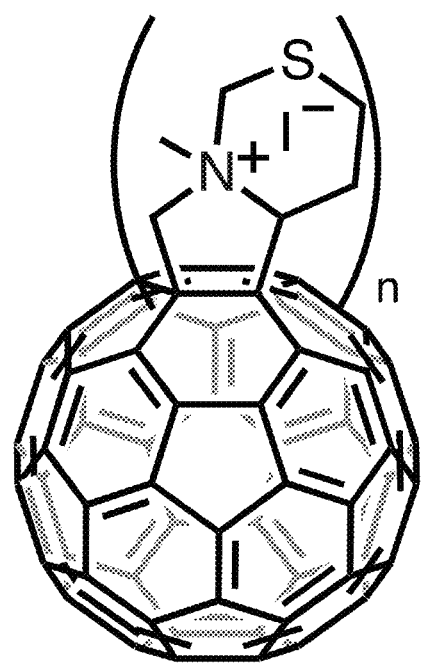
FIG. 13. Illustration of Formula I.
Figure 14:
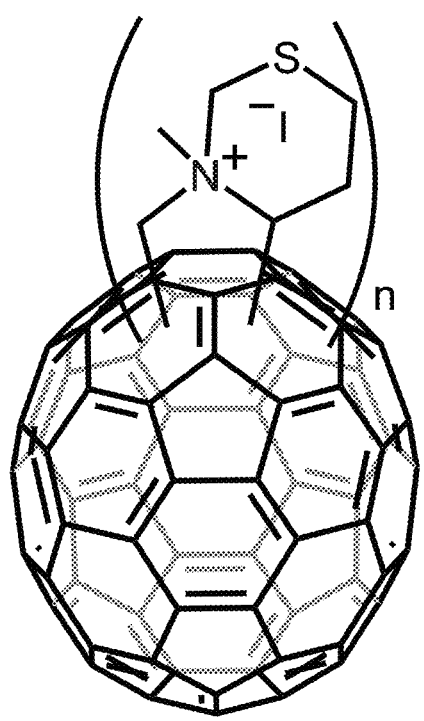
FIG. 14. Illustration of Formula II.
Figure 15:
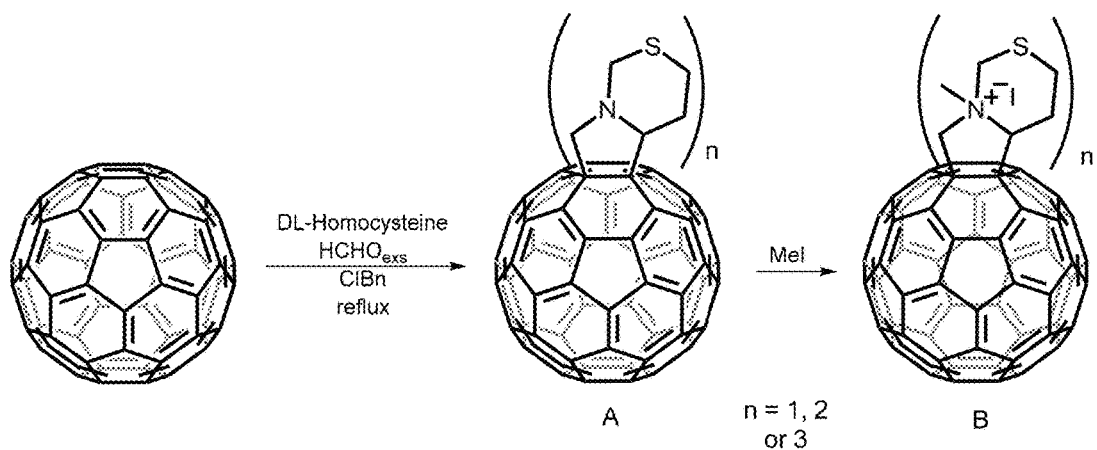
FIG. 15. Scheme showing synthesis of tetrahydro-1H—$C_{60}$-fulleropyrrolidinium[1,2-c][1,3]thiazine iodide B. tetrahydro-1H—$C_{60}$-fulleropyrrolo[1,2-c][1,3]thiazine A (0.01 mmol) was dissolved in methyl iodide (5 mL) and stirred for 36 h at room temperature to give a black precipitate.
Figure 16:
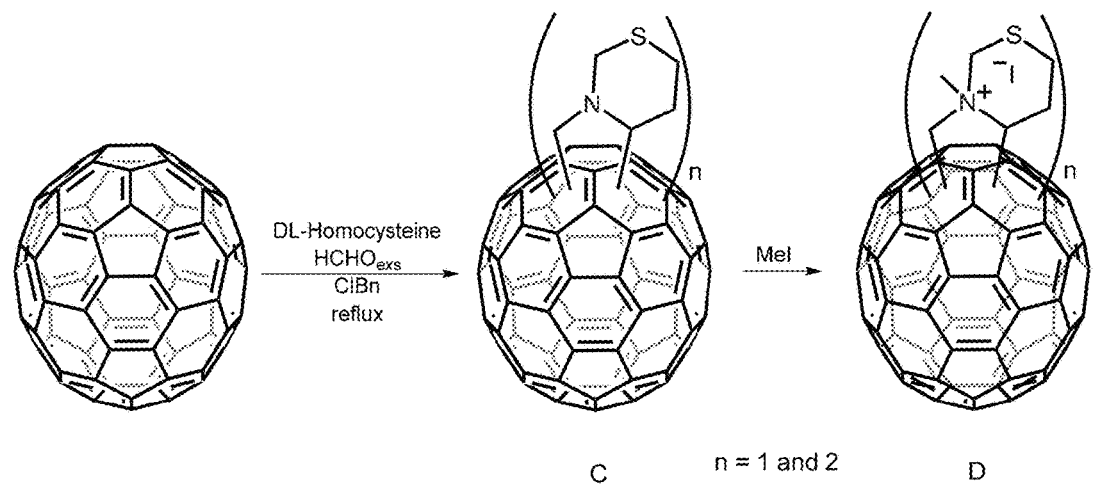
FIG. 16. Synthesis of tetrahydro-1H—$C_{70}$-fulleropyrrolidinium[1,2-c][1,3]thiazine iodide D. tetrahydro-1H—$C_{70}$-fulleropyrrolo[1,2-c][1,3]thiazine C (0.01 mmol) was dissolved in methyl iodide (5 mL) and stirred for 36 h at room temperature to give a black precipitate. The solvent was dried and the precipitate was washed with $CS_2$, $CHCl_3$, toluene, MeOH and acetone in this order; to afford a black powder, [1,3]thiazine[70]fulleropyrrolidinium iodide D. The yields were 79% for n=1 and 71% for n=2.

The inventors have designed and synthesized new fullerene derivatives that can effectively inhibit an HIV protease. As a result, a new class of fullerene derivatives, [1,3]thiazinefulleropyrrolo and their pyrrolidinium salts, were prepared (FIG. 1 and FIG. 2). The pyrrolidinium salts were tested for their activity against the HIV protease. Studies demonstrate that the [60]-derivatives exhibit potent inhibition of late stage HIV. The infectivity was determined to be less than 2% using DMSO as the 100% infectivity control (FIG. 3). These results suggest that this new class of fullerene derivatives can be used for the effective treatment of HIV patients.

Certain aspects described herein are directed to treatment for the human immunodeficiency virus (HIV) by administering $C_{60}$ or $C_{70}$ fullerene derivatives. HIV is a pathogenic retrovirus and the causative agent of acquired immune deficiency syndrome (AIDS) and related disorders (Barre-Sinossi et al., 1983, Science 220:868-870; Gallo et al., 1984, Science 224:500-503). There are at least two distinct types of HIV: HIV-1 (Barre-Sinossi et al., 1983, Science 220:868-870; Gallo et al., 1984, Science 224:500-503) and HIV-2 (Clavel et al., 1986, Science 223:343-346; Guyader et al., 1987, Nature 326:662-669). Further, a large amount of genetic heterogeneity exists within populations of each of these types. Infection of human CD-4+ T-lymphocytes with an HIV virus leads to depletion of the cell type and eventually to opportunistic infections, neurological dysfunctions, neoplastic growth, and untimely death.

HIV is a member of the lentivirus family of retroviruses (Teich et al., 1984, RNA Tumor Viruses, Weiss et al., eds., CSH-press, pp. 949-956). Retroviruses are small enveloped viruses that contain a diploid, single-stranded RNA genome, and replicate via a DNA intermediate produced by a virally-encoded reverse transcriptase, an RNA-dependent DNA polymerase (Varmus 1988, Science 240:1427-1439). The HIV viral particle consists of a viral core, made up of proteins designated p24 and p18. The viral core contains the viral RNA genome and those enzymes required for replicative events. Myristylated gag protein forms an outer viral shell around the viral core, which is, in turn, surrounded by a lipid membrane envelope derived from the infected cell membrane. The HIV envelope surface glycoproteins are synthesized as a single 160 kD precursor protein which is cleaved by a cellular protease during viral budding into two glycoproteins, gp41 and gp120. gp41 is a transmembrane protein and gp120 is an extracellular protein which remains noncovalently associated with gp41, possibly in a trimeric or multimeric form (Hammerwskj old and Rekosh, 1989, Biochem. Biophys. Acta 989:269-280).

HIV is targeted to CD4+ T lymphocytes because the CD4 surface protein acts as the cellular receptor for the HIV-1 virus (Dalgleish et al., 1984, Nature 312: 767-768, Maddon et al., 1986, Cell 47:333-348). Viral entry into cells is dependent upon gp120 binding the cellular CD4+ receptor molecules, while gp41 anchors the envelope glycoprotein complex in the viral membrane (McDougal et al., 1986, Science 231:382-385; Maddon et al., 1986, Cell 47:333-348) and thus explains HIV's tropism for CD4+ cells.

Fullerenes are carbon compounds composed entirely of carbon, in the form of a hollow sphere, ellipsoid, tube, or other shapes. Cylindrical fullerenes are called carbon nanotubes and spherical fullerenes are sometimes referred to as "buckyballs." $C_{70}$ fullerene or [70]fullerene is a cage like molecule composed of 70 carbon atoms joined together by single and double bonds to form a hollow sphere with 25 hexogonal and 12 pentagonal rings. The rings of the [70] fullerene can be chemically modified. In certain aspects [70]fullerenes can be modified with pyrrolidines.

In certain embodiments described herein fullerenes and derivatives thereof can have antiviral activity and can be used for treatment of viral infections, such as HIV-infection. Fullerenes derivatives can be designed to bind or interact with and inhibit HIV protease, which is essential for HIV lifecycle. Inhibiting HIV protease inhibits HIV replication and infection.

Methods for making the fullerene derivative described herein comprise, but are not limited to mixing $C_{60}$ or $C_{70}$ fullerene, DL-Homocysteine, and paraformaldehyde in chlorobenzene. The resulting mixture was dissolved with sonication and refluxed overnight under $N_2$ gas atmosphere. After this time, the solvent was removed under reduced pressure and the mixture chromatographed using silica gel. Carbon disulfide ($CS_2$) was used as the mobile phase to elute the unreacted $C_{70}$, the polarity was then increased using $CS_2$:$CHCl_3$ (1:1) to elute the desire mono-adducts (F1: gamma-1; F2: beta-1; F3: gamma-2, beta-2-, alpha-1).

Various chemical definitions related to such compounds are provided as follows.

As used herein, the term "halo" designates —F, —Cl, —Br or —I.

The term "alkyl," by itself or as part of another substituent, means, unless otherwise stated, a linear (i.e. unbranched) or branched carbon chain, which may be fully saturated, mono- or polyunsaturated.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of S and N. The heteroatom(s) may be placed at any interior position of the heteroalkyl group or at the position at which the alkyl group is attached to the remainder of the molecule. Up to two heteroatoms may be consecutive.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule. Pyrrolidine, also known as tetrahydropyrrole, is a saturated heterocycle with the molecular formula $(CH_2)_4NH$, a cyclic secondary amine. A thiazine moiety is a 6 membered heterocylic moiety containing a ring of four carbon, one nitrogen and one sulfur atom.

The term "aryl" means a polyunsaturated, aromatic, hydrocarbon substituent. Aryl groups can be monocyclic or polycyclic (e.g., 2 to 3 rings that are fused together or linked covalently). One example of a polycyclic compound is the fullerenes. A fullerene is a molecule of carbon in the form of a hollow sphere, ellipsoid, tube, and many other shapes. Spherical fullerenes are also called buckyballs. Cylindrical ones are called carbon nanotubes or buckytubes. Fullerenes are similar in structure to graphite, which is composed of stacked graphene sheets of linked hexagonal rings; but they may also contain pentagonal (or sometimes heptagonal) rings. The discovery of fullerenes greatly expanded the number of known carbon allotropes, which until recently were limited to graphite, diamond, and amorphous carbon such as soot and charcoal.

A particular fullerene is the $C_{70}$ fullerene. The $C_{70}$ fullerene consists of 70 carbon atoms. It is a cage-like fused-ring structure made of 25 hexagons and 12 pentagons, with a carbon atom at the vertices of each polygon and a bond along each polygon edge.

In certain aspects a thiazine moiety is used as a substituent to a pyrrolidine group on a $C_{60}$ or $C_{70}$ fullerene as described herein.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well.

A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

A regioisomer is where a functional group or other substituent changes position on a parent structure. For example, a hydroxyl group can occupy three different positions on an n-pentane chain forming three different compounds or a pyrrolidine can occupy different positions on a fullerene.

Pharmaceutical compositions of the invention are useful in the treatment or prevention of viral infections in humans and contain as an active agent one or more isoform of tetrahydro-1H—$C_{60}$-fulleropyrrolo[1,2-c][1,3]thiazine salt derivatives (Formula I) or tetrahydro-1H—$C_{70}$-fulleropyrrolo[1,2-c][1,3]thiazine salt derivatives (Formula II). In certain aspects the pharmaceutical compositions contain at least one other antiviral agent, such as reverse transcriptase inhibitors, protease inhibitor, inhibitors of mRNA processing, inhibitors of protein glycosylation and inhibitors of viral fusion. Such agents include but are not limited to nucleoside analogs or chain terminators (e.g., dideoxynucleosides). Additional suitable therapeutic agents which may be used in combinational therapy include, but are not limited to 2-deoxy-D-glucose (2-dGlc), deoxynojirimycin, acycloguanosine, ribavirin (virazole), rifampicin (rifadin), adamantidine, rifabutine, ganciclover, (DHPG), fluoroiodoaracytosine, idoxurine, trifluorothymidine, adenine arabinoside (ara-A), ara-AMP, bromovinyldeoxyuridine, bromovinylarauracil (BV-araU by Bristol-Meyers Squibb (1-beta-D-arabinofuranoside-E-5-[2-bromovinyl]uracil)) rimantadine, arildone, diarylamidine, (S)-(p-nitrobenzyl-)6-thioinosine and phosphonoformate.

The compounds and compositions described herein may be administered using techniques well known to those in the art. Preferably, agents are formulated and administered systemically. Techniques for formulation and administration may be found in "Remington's Pharmaceutical Sciences", 18th ed., 1990, Mack Publishing Co., Easton, Pa. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. In certain aspects administration is intravenous. For injection, the agents of the invention may be formulated in aqueous solutions, preferably in physiologically compatible buffers such as Hanks' solution, Ringer's solution, or physiological saline buffer.

A therapeutically effective dose refers to that amount of the compound sufficient to result in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population).

Pharmaceutical compositions containing the compounds described herein can be administered to a human patient, by itself, or in pharmaceutical compositions where it is mixed with suitable carriers or excipient(s) at doses to treat a viral infection, in particular HIV infection. Techniques for formulation and administration of the compounds of the instant application may be found in "Remington's Pharmaceutical Sciences," Mack Publishing Co., Easton, Pa., latest edition.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections; transdermal, topical, vaginal and the like. Dosage forms include but are not limited to tablets, troches, dispersions, suspensions, suppositories, solutions, capsules, creams, patches, minipumps and the like.

Pharmaceutical compositions for use in accordance with the present invention thus may be formulated in conventional manner using one or more physiologically acceptable carriers comprising excipients and auxiliaries, which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The antiviral activity exhibited by the compounds described herein may be measured, for example, by easily performed in vitro assays.

For the compounds of the present invention, alone or as part of a pharmaceutical composition, such doses are between about 0.001 mg/kg and 1 mg/kg body weight, preferably between about 1 and 100 µg/kg body weight, most preferably between 1 and 10 µg/kg body weight.

Therapeutically effective doses will be easily determined by one of skill in the art and will depend on the severity and course of the disease, the patient's health and response to treatment, the patient's age, weight, height, sex, previous medical history and the judgment of the treating physician.

In certain aspects a patient may have an HIV infection or be at risk of developing an HIV infection, or has been exposed to HIV. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

It is contemplated that any embodiment discussed in this specification can be implemented with respect to any method or composition of the invention, and vice versa. Furthermore, compositions of the invention can be used to achieve methods of the invention.

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Mono-, Bis- and Tris-[1,3]Thiazine[60]Fulleropyrrolidine

To a 250 mL round bottom flask were added $C_{60}$ (100 mg, 0.14 mmol), DL-Homocysteine (16 mg, 0.12 mmol) and paraformaldehyde (36 mg, 1.2 mmol) followed by 100 mL of chlorobenzene. The resulting mixture was dissolved with sonication and refluxed overnight under $N_2$ gas atmosphere. After this time, the solvent was removed under reduced pressure and the mixture chromatographed using silica gel. Carbon disulfide ($CS_2$) was used as the mobile phase to elute the unreacted $C_{60}$, the polarity was then increased using chloroform ($CS_2$:$CHCl_3$ 10%, 30%, 50%, 75%) to elute the desire mono-, bis- and tris-adducts.

Mono-[1,3]Thiazine[60]Fulleropyrrolidine. $^1$H NMR (600 MHz, $CS_2$:$CDCl_3$): δ (ppm)=4.98 (d, 1H), 4.49-4.46 (dd, 1H), 4.27 (d, 1H), 4.20 (d, 1H), 3.96-3.94 (dd, 1H), 3.20-3.15 (dt, 1H), 3.09-3.07 (m, 1H), 2.92-2.90 (dd, 1H), 2.69-2.63 (dq, 1H). UV-vis $\lambda_{max}$ (nm): MALDI-TOF MS (m/z): calcd. 835.046, found 834.120 [M−H].

Bis-[1,3]Thiazine[60]Fulleropyrrolidine. MALDI-TOF MS (m/z): calcd. 950.091, found 950.071 [M]$^+$.

Tris-[1,3]Thiazine[60]Fulleropyrrolidine. MALDI-TOF MS (m/z): calcd. 1065.137, found 1066.069 [M+H]$^+$.

Example 2

Synthesis of Mono- and Bis-[1,3]Thiazine[70]Fulleropyrrolidine

To a 250 mL round bottom flask were added $C_{70}$ (100 mg, 0.12 mmol), DL-Homocysteine (14 mg, 0.10 mmol) and paraformaldehyde (30 mg, 1.0 mmol) followed by 100 mL of chlorobenzene. The resulting mixture was dissolved with sonication and refluxed overnight under $N_2$ gas atmosphere. After this time, the solvent was removed under reduced pressure and the mixture chromatographed using silica gel. Carbon disulfide ($CS_2$) was used as the mobile phase to elute the unreacted $C_{70}$, the polarity was then increased using $CS_2$:$CHCl_3$ (1:1) to elute the desire mono-adducts (F1: gamma-1; F2: beta-1; F3: gamma-2, beta-2-, alpha-1).

Mono-[1,3]Thiazine[70]-$\gamma^1$-fulleropyrroldine. $^1$H NMR (600 MHz, $CS_2$:$CDCl_3$) δ (ppm): 4.48 (d, 1H), 4.09 (dd, 1H), 3.72 (m, 2H), 3.55 (s, 2H), 2.87 (m, 1H), 2.69-2.66 (m, 1H). UV-vis ($CHCl_3$) $\lambda_{max}$ (nm): 330, 400, 514, 641, 743. MALDI-TOF MS (m/z): calcd. 955.046 [M]+, found 955.071 [M]+.

Mono-[1,3]Thiazine[70]-$\beta^1$-fulleropyrrolidine. $^1$H NMR (600 MHz, $CS_2$:$CDCl_3$) δ (ppm): 4.06-4.04 (dd, 1H), 4.03 (d, 1H), 3.42 (d, 1H), 2.88-2.84 (m, 1H), 2.78-2.76 (m, 1H), 2.42 (m, 1H), 1.74-1.68 (m, 1H). UV-vis ($CHCl_3$) $\lambda_{max}$ (nm): 324, 366, 401, 440, 582, 640, 694. MALDI-TOF MS (m/z): calcd. 955.046 [M]$^+$, found 955.071 [M]$^+$.

Mono-[1,3]Thiazine[70]-$\gamma^2$-fulleropyrrolidine. $^1$H NMR (600 MHz, $CS_2$:$CDCl_3$) δ (ppm): 4.18 (d, 1H), 4.04 (d, 1H), 3.38 (d, 1H), 2.84 (d, 1H), 2.72-2.67 (m, 1H), 2.65 (d, 1H), 2.41-2.35 (m, 1H), 1.90 (dd, 1H).

Mono-[1,3]Thiazine[70]-$\beta^2$-fulleropyrrolidine. $^1$H NMR (600 MHz, $CS_2$:$CDCl_3$) δ (ppm): 4.23 (d, 1H), 4.16 (d, 1H), 4.06-4.03 (m, 1H), 3.83 (d, 1H), 3.42 (d, 1H), 3.14 (d, 1H).

Mono-[1,3]Thiazine[70]-$\alpha^1$-fulleropyrrolidine. $^1$H NMR (600 MHz, $CS_2$:$CDCl_3$) δ (ppm): 4.27 (dd, 1H), 4.17 (m, 1H), 3.97 (m, 1H), 3.59 (d, 1H), 3.33 (d, 1H), 2.90-2.87 (m, 1H), 2.55 (m, 1H), 2.47 (dd, 1H), 2.24-2.22 (m, 1H).

Example 3

Synthesis of the Quaternary Ammonium Fullerene Salts

Synthesis of tetrahydro-1H—$C_{60}$-fulleropyrrolidinium[1,2-c][1,3]thiazine iodide B. tetrahydro-1H—$C_{60}$-fulleropyrrolo[1,2-c][1,3]thiazine A (0.01 mmol) was dissolved in methyl iodide (5 mL) and stirred for 36 h at room temperature to give a black precipitate. The solvent was dried and the precipitate was washed with $CS_2$, $CHCl_3$, toluene, MeOH and acetone in this order; to afford a brown powder, [1,3]thiazine[60]fulleropyrrolidinium iodide B. The yields were 65% for n=1, 74% for n=2 and 75% for n=3.

Synthesis of tetrahydro-1H—$C_{70}$-fulleropyrrolidinium[1,2-c][1,3]thiazine iodide D. tetrahydro-1H—$C_{70}$-fulleropyrrolo[1,2-c][1,3]thiazine C (0.01 mmol) was dissolved in methyl iodide (5 mL) and stirred for 36 h at room temperature to give a black precipitate. The solvent was dried and the precipitate was washed with $CS_2$, $CHCl_3$, toluene, MeOH and acetone in this order; to afford a black powder, [1,3]thiazine[70]fulleropyrrolidinium iodide D. The yields were 79% for n=1 and 71% for n=2.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition comprising tetrahydro-1H-$C_{60}$-fullero[pyrrolo[1,2-c][1,3]thiazine]$_n$ salt derivatives or tetrahydro-1H-$C_{70}$-fullero[pyrrolo[1,2-c][1,3]thiazine]$_n$ salt derivatives.

2. The composition of claim 1, wherein the tetrahydro-1H—$C_{70}$-fulleropyrrolo[1,2-c][1,3]thiazine salt is α tetrahydro-1H—$C_{70}$-fulleropyrrolo[1,2-c][1,3]thiazine salt.

3. The composition of claim 1, wherein the tetrahydro-1H—$C_{70}$-fulleropyrrolo[1,2-c][1,3]thiazine salt is β tetrahydro-1H—$C_{70}$-fulleropyrrolo[1,2-c][1,3]thiazine salt.

4. The composition of claim 1, wherein the tetrahydro-1H—$C_{70}$-fulleropyrrolo[1,2-c][1,3]thiazine salt is γ tetrahydro-1H—$C_{70}$-fulleropyrrolo[1,2-c][1,3]thiazine salt.

5. The composition of claim 1, wherein the tetrahydro-1H—$C_{70}$-fulleropyrrolo[1,2-c][1,3]thiazine salt is δ tetrahydro-1H—$C_{70}$-fulleropyrrolo[1,2-c][1,3]thiazine salt.

6. A tetrahydro-1H—$C_{60}$-fulleropyrrolo[1,2-c][1,3]thiazine or tetrahydro-1H—$C_{70}$-fulleropyrrolo[1,2-c][1,3]thiazine salt prepared by:
   (a) mixing $C_{60}$ or $C_{70}$ fullerene, DL-Homocysteine, and paraformaldehyde in chlorobenzene;
   (b) dissolving the $C_{60}$ or $C_{70}$ fullerene, DL-Homocysteine, and paraformaldehyde with sonication;
   (c) refluxing the dissolved mixture under $N_2$ gas atmosphere;
   (d) removing chlorobenzene under reduced pressure;
   (e) isolating reaction products from reagents by chromatography;
   (f) reacting the [60] or [70] tetrahydro-1H-fulleropyrrolo[1,2-c][1,3]thiazine derivatives with iodomethane at room temperature;
   (g) removing iodomethane under reduced pressure; and
   (h) washing the [1,3]thiazinefulleropyrrolidinium iodide salts with $CS_2$, $CHCl_3$, toluene, MeOH and acetone.

7. A method for treating a HIV patient comprising administering to a patient an effective amount of a one or more isomers of tetrahydro-1H—$C_{60}$-fulleropyrrolo[1,2-c][1,3]thiazine or tetrahydro-1H—$C_{70}$-fulleropyrrolo[1,2-c][1,3]thiazine salts.

8. The method of claim 7, wherein the HIV patient has a second viral infection.

9. The method of claim 8, wherein the second viral infection is hepatitis B virus, hepatitis C virus, or cytomegalovirus.

10. The method of claim 7, wherein the patient is co-infected with hepatitis B virus, hepatitis C virus, or cytomegalovirus.

* * * * *